(12) United States Patent
Gibertoni et al.

(10) Patent No.: US 11,103,677 B2
(45) Date of Patent: Aug. 31, 2021

(54) COAXIAL DRAINING TUBE, PARTICULARLY FOR CHEST DRAINING SYSTEMS

(71) Applicant: REDAX S.p.A., Poggio Rusco (IT)

(72) Inventors: Andrea Gibertoni, San Possidonio (IT); Lucio Gibertoni, Mirandola (IT)

(73) Assignee: REDAX S.P.A., Poggio Rusco (IT)

( * ) Notice: Subject to any disclaimer, the term of this patent is extended or adjusted under 35 U.S.C. 154(b) by 414 days.

(21) Appl. No.: 15/512,355

(22) PCT Filed: Aug. 27, 2015

(86) PCT No.: PCT/EP2015/069655
§ 371 (c)(1),
(2) Date: Mar. 17, 2017

(87) PCT Pub. No.: WO2016/041762
PCT Pub. Date: Mar. 24, 2016

(65) Prior Publication Data
US 2017/0209669 A1 Jul. 27, 2017

(30) Foreign Application Priority Data
Sep. 17, 2014 (IT) .......................... MI2014A001601

(51) Int. Cl.
*A61M 5/00* (2006.01)
*A61M 25/00* (2006.01)
(Continued)

(52) U.S. Cl.
CPC .......... *A61M 25/007* (2013.01); *A61M 1/008* (2013.01); *A61M 25/00* (2013.01);
(Continued)

(58) Field of Classification Search
CPC ........ A61M 5/00; A61M 25/00; A61M 31/00; A61M 25/16; A61M 39/02; A61M 27/00;
(Continued)

(56) References Cited

U.S. PATENT DOCUMENTS 2,930,378 A 3/1960 Buyers
3,771,527 A 11/1973 Ruisi
(Continued)

FOREIGN PATENT DOCUMENTS

DE 3325920 A1 2/1985

OTHER PUBLICATIONS

International Search Report dated Nov. 2, 2015 re: Application No. PCT/EP2015/069655, pp. 1-3, citing: U.S. Pat. No. 6,299,593 B1, U.S. Pat. No. 3,771,527 A, U.S. Pat. No. 2,930,378 A, DE 33 25 920 A1.
(Continued)

*Primary Examiner* — Tatyana Zalukaeva
*Assistant Examiner* — Ilya Y Treyger
(74) *Attorney, Agent, or Firm* — Cantor Colburn LLP

(57) ABSTRACT

A coaxial draining tube, particularly for chest draining systems, includes an inner tube, which has a first opening, and an outer tube, which has a second opening. The inner tube is enclosed within the outer tube and has a smaller diameter than the second opening of the outer tube. The first and second tubes are mutually coupled by way of a supporting component and include one or more holes adapted to allow the passage of air from the chest cavity to the first opening of the inner tube and one or more holes adapted to allow the passage of liquids from the chest cavity to the second opening of the outer tube. The one or more holes are provided in the portion of the coaxial draining tube that is intended to be inserted in the chest cavity of a patient.

4 Claims, 3 Drawing Sheets

(51) Int. Cl.
*A61M 27/00* (2006.01)
*A61M 1/00* (2006.01)
*A61M 31/00* (2006.01)
*A61M 25/16* (2006.01)
*A61M 39/02* (2006.01)

(52) U.S. Cl.
CPC ........ *A61M 25/0067* (2013.01); *A61M 27/00* (2013.01); *A61M 2025/0039* (2013.01); *A61M 2210/101* (2013.01)

(58) Field of Classification Search
CPC ................ A61M 25/007; A61M 1/008; A61M 25/0067; A61M 2025/0039; A61M 2210/101; A61K 9/02
See application file for complete search history.

(56) References Cited

U.S. PATENT DOCUMENTS 4,423,740 A * 1/1984 Castle ...................... A61B 5/03
600/561
6,299,593 B1 10/2001 Wakabayashi

OTHER PUBLICATIONS

EP Examination Report dated Mar. 24, 2021 re: Application No. 15 759 707.1, pp. 1-5.

* cited by examiner

COAXIAL DRAINING TUBE, PARTICULARLY FOR CHEST DRAINING SYSTEMS

TECHNICAL FIELD

The present disclosure relates to a coaxial draining tube, particularly but not exclusively useful and practical in the field of the patient circuit of a chest draining system, the latter having the fundamental goal of evacuating air and/or liquids, formed following surgery or traumas, from the chest cavity of a patient, in order to avoid their accumulation.

BACKGROUND

In general, a chest draining tube is a flexible tube provided by using transparent and sterile plastic materials, such as for example PVC (polyvinyl chloride) or silicone; said tube is inserted, through an incision, in the chest of the patient until it reaches the pleural space in the chest cavity.

Said draining tube constitutes the distal element of a chest draining system and is therefore used to reach and remove fluids, i.e., air and/or liquids, accumulated in the chest cavity; in particular, usually, air tends to accumulate in the apical region of the chest cavity of the patient, while liquids, such as for example blood, tend to accumulate in the basal region of the chest cavity of the patient.

Currently, various types of draining tubes, particularly for chest draining systems, are known. One of these chest draining tubes of the known type has a plurality of holes in its end portion, which is arranged in the apical region of the chest cavity of the patient, thus allowing the immediate exit of the air toward the collecting chamber, with the liquids that instead remain deposited in the basal region of the chest cavity.

By using this known chest draining tube, the evacuation of the liquids, deposited initially in the basal region of the chest cavity, therefore occurs when the lung, by expanding due to the exit of the air, pushes said liquids toward the apical region of the chest cavity proper, i.e., toward the holes that are present in the end portion of the draining tube and therefore toward the exit and the collecting chamber.

It is clear that when using this chest draining tube of the known type, provided with holes in its end portion, the air and the liquids that are present in the chest cavity of the patient are evacuated in an alternated and non-simultaneous manner, since the air exits in a first step while the liquids exit only in a second step.

A different chest draining tube of the known type has, instead of holes in the end portion, one or more grooves that are longitudinal with respect to the chest draining tube. This type of draining tube has been devised in an attempt to allow the simultaneous evacuation of air and liquids from the chest cavity of the patient by using a single draining tube, but in this case the liquids exit immediately from the basal region of the chest cavity and the air exits from the apical region of said chest cavity only afterwards.

It is thus clear that even by using said grooved chest draining tube of the known type the simultaneous exit of the air and liquids present in the chest cavity of the patient does not occur, since the liquids exit in a first step while the air exits only in a second step.

One solution to the drawback described above, related to the evacuation from the chest cavity of the patient of air and liquids in two distinct and alternated steps, entails the placement of a pair of draining tubes, both having a plurality of holes in their end portion, inside the chest cavity, particularly one in the apical region and another in the basal region.

The first draining tube, arranged in the apical region, allows the evacuation of the air, while the second draining tube, arranged in the basal region, allows the evacuation of the liquids. Both draining tubes then converge in a three-way or Y-shaped connector and the fluids transported thereby continue toward the collecting chamber in a single tube.

By using a pair of known chest draining tubes, therefore, the air and the liquids that are present in the chest cavity of the patient can be evacuated in a simultaneous manner.

In view of the above, these currently known chest draining tubes are not devoid of drawbacks, which include the fact that if they are used individually they do not allow the simultaneous and continuous evacuation of the air and of the liquids present in the chest cavity of the patient.

Another drawback of these conventional chest draining tubes is that since they do not allow continuous evacuation of the air in the collecting chamber, in practice they prevent medical staff from seeing immediately any air losses of the patient.

A further drawback of these conventional chest draining tubes is that the only manner to ensure the simultaneous and continuous evacuation of air and liquids present in the chest cavity of the patient is to use a pair of known draining tubes; however, this solution leads to a significant increase in the intensity of the pain felt by the patient and to additional difficulties in the already complex management of the chest draining system.

The aim of the present disclosure is to overcome the limitations of conventional art described above, by devising a coaxial draining tube, particularly for chest draining systems, that allows to obtain similar or better effects than those obtainable with chest draining tubes of the conventional type, allowing the simultaneous and continuous evacuation of the fluids, i.e., of the air and of the liquids, present in the chest cavity of the patient, though being used individually.

SUMMARY

Within this aim, the disclosure devises a coaxial draining tube, particularly for chest draining systems, that facilitates a faster expansion of the lung by way of the simultaneous evacuation of air and liquids, with the consequent reduction of hospitalization time of the patient.

The present disclosure also devises a coaxial draining tube, particularly for chest draining systems, that facilitates the management thereof and, more generally, the management of the chest draining system.

The present disclosure further devises a coaxial draining tube, particularly for chest draining systems, that minimizes the intensity of the pain felt by the patient, as well as the possibility of external contamination of the patient, since it is a single draining tube.

The present disclosure provides a coaxial draining tube, particularly for chest draining systems, that allows a continuous evacuation of air in the collecting chamber, allowing medical staff to view immediately any air losses of the patient and providing medical staff with additional information on the air losses of the patient.

The present disclosure also devises a coaxial draining tube, particularly for chest draining systems, that allows to reduce the workload of medical staff and nurses.

The present disclosure further provides a coaxial draining tube, particularly for chest draining systems, that is highly reliable, relatively easy to provide and at low costs.

These aims and advantages that will become better apparent hereinafter are achieved by providing a coaxial draining tube, particularly for chest draining systems, wherein the coaxial draining tube comprises an inner tube having a first opening, and an outer tube having a second opening, said inner tube being enclosed within said outer tube and having a smaller diameter than the diameter of said second opening of said outer tube, said first tube and second tube being mutually coupled by way of supporting means and comprising one or more holes adapted to allow the passage of air from the chest cavity to said first opening of said inner tube and one or more holes adapted to allow the passage of liquids from the chest cavity to said second opening of said outer tube, said one or more holes being provided in the portion of said coaxial draining tube that is intended to be inserted in the chest cavity of a patient.

BRIEF DESCRIPTION OF THE DRAWINGS

Further characteristics and advantages of the disclosure will become better apparent from the description of a preferred but not exclusive embodiment of the coaxial draining tube according to the disclosure, illustrated by way of non-limiting example in the accompanying drawings, wherein.

DETAILED DESCRIPTION OF THE DRAWINGS

Figure 1:
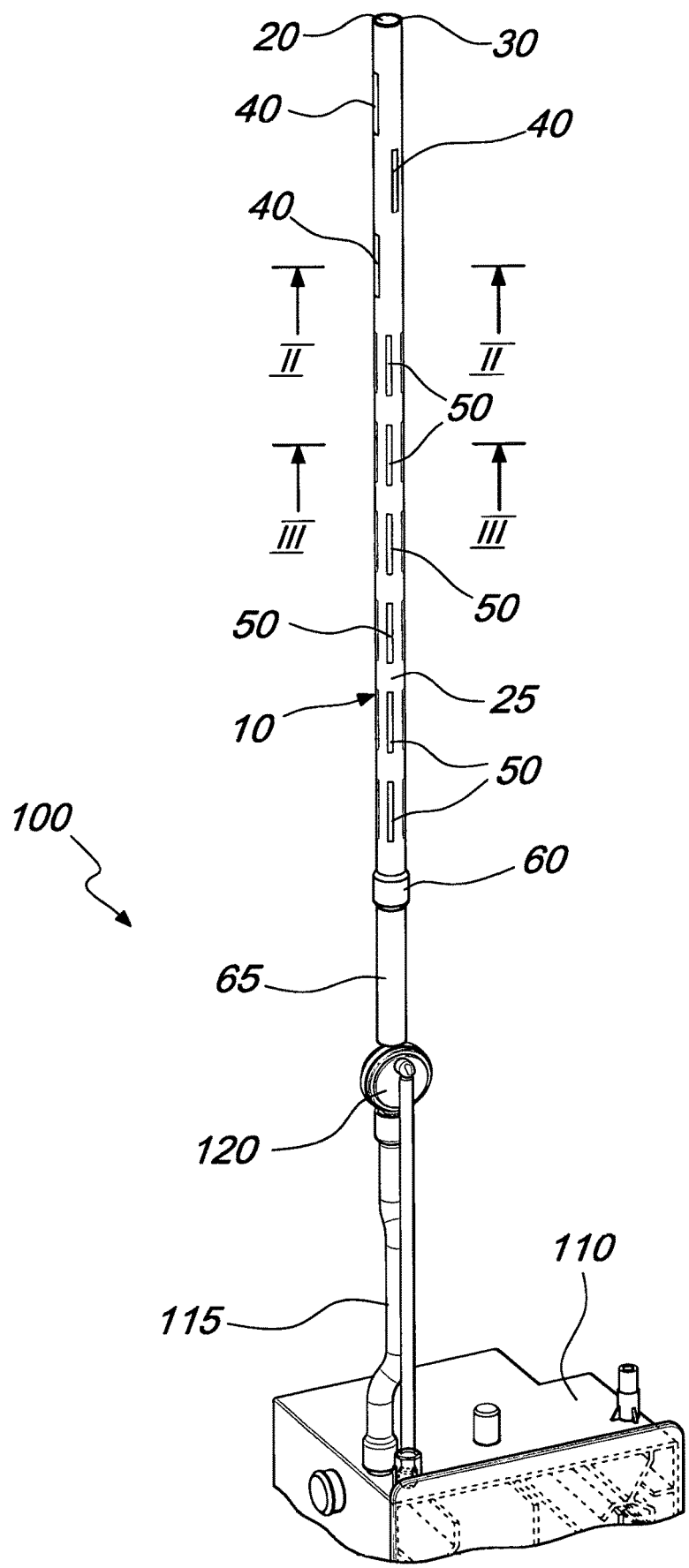
FIG. 1 is a perspective view of a chest draining system that uses an embodiment of the coaxial draining tube, particularly for chest draining, according to the present disclosure.
Figure 2:
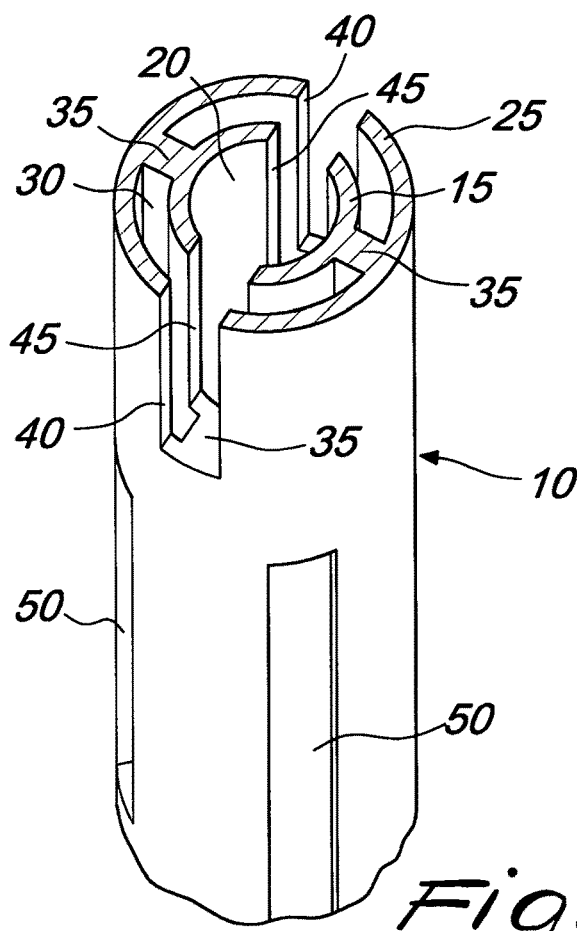
FIG. 2 is a perspective view of a first cross-section of an embodiment of the coaxial draining tube, particularly for chest draining, according to the present disclosure.
Figure 3:
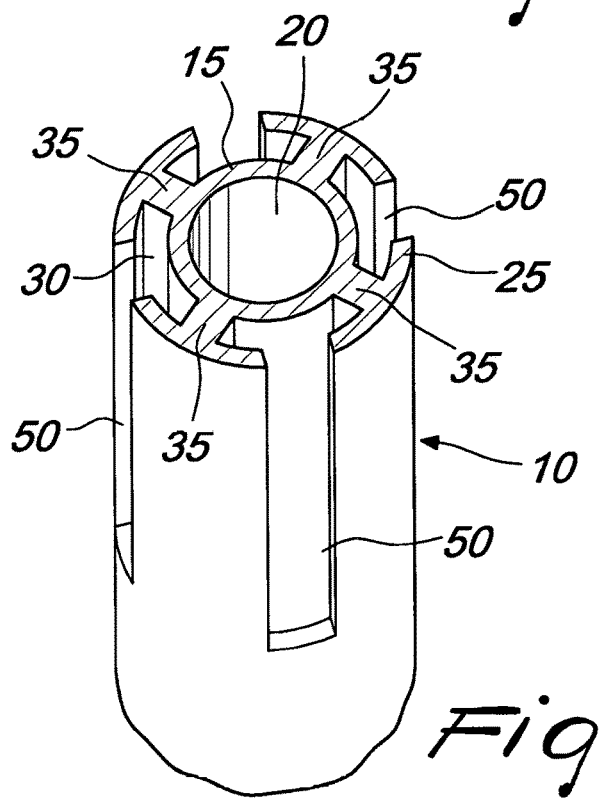
FIG. 3 is a perspective view of a second cross-section of an embodiment of the coaxial draining tube, particularly for chest draining, according to the present disclosure.
Figure 4:
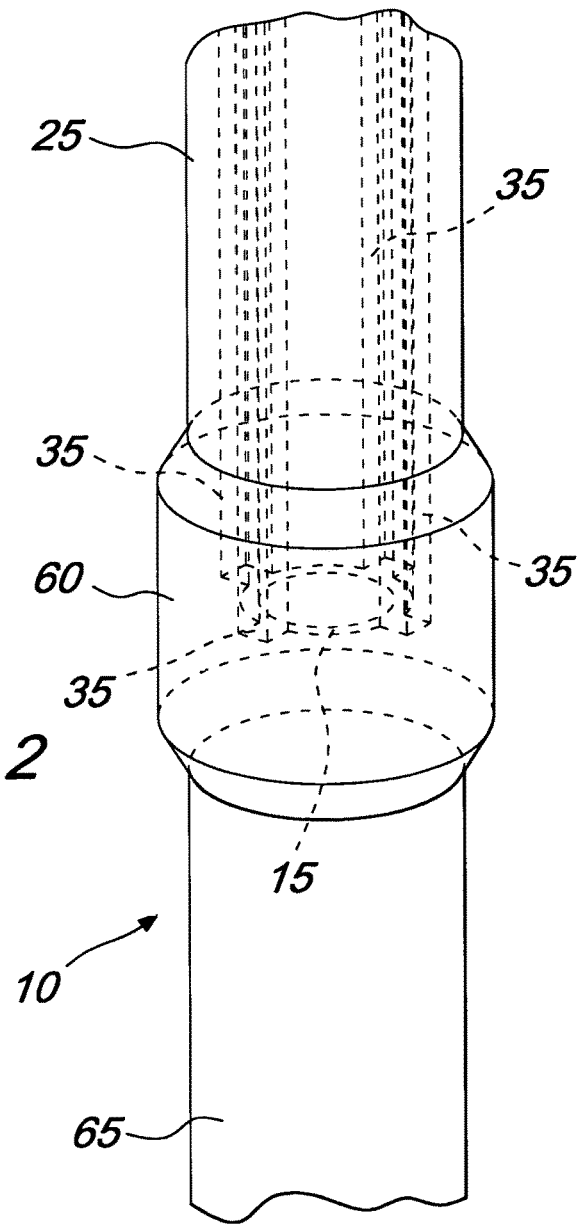
FIG. 4 is a view of the connector of an embodiment of the coaxial draining tube, particularly for chest draining, according to the present is disclosure.
Figure 5:
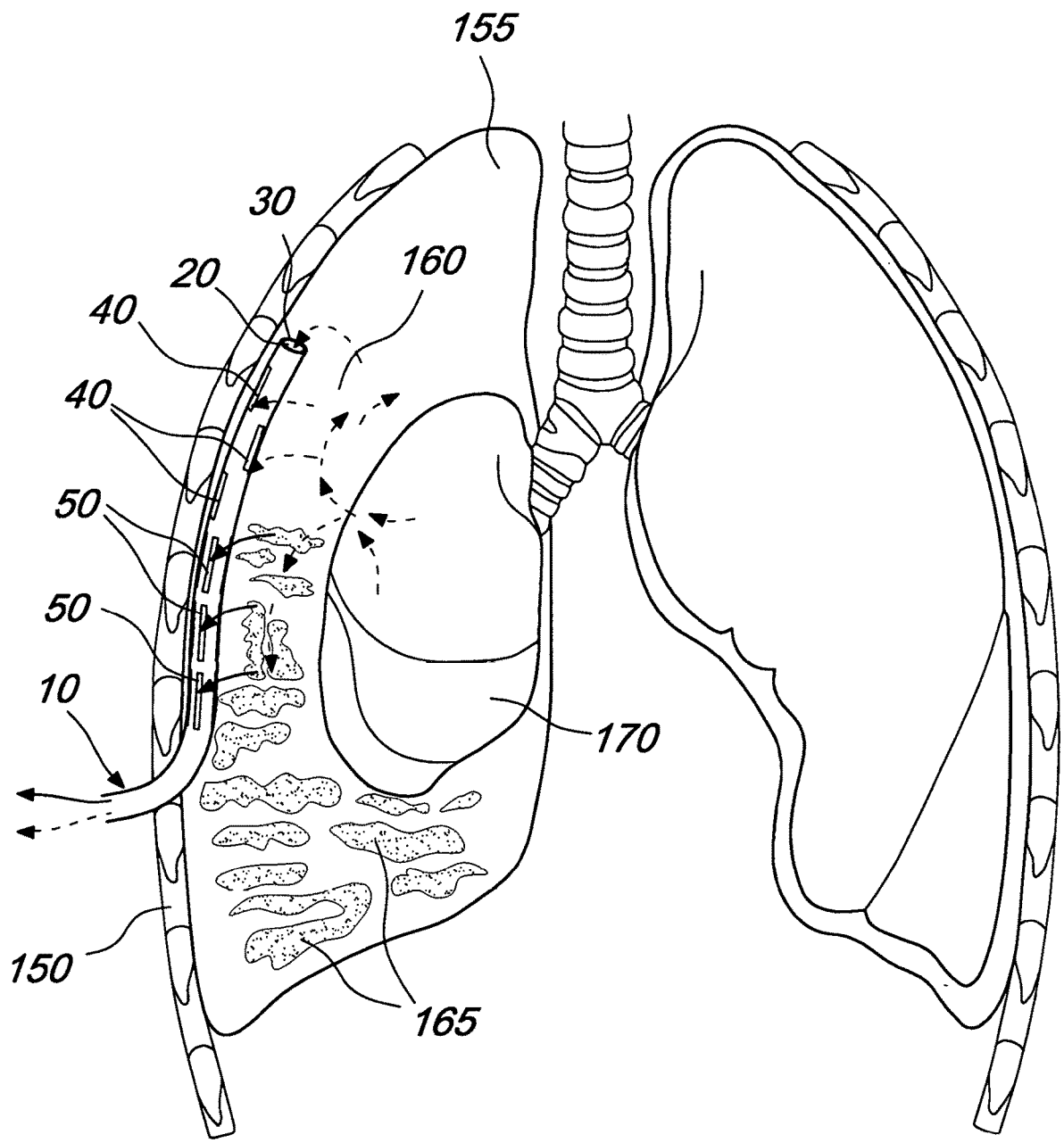
FIG. 5 is a schematic view of the placement in the chest cavity and of the operation of an embodiment of the coaxial draining tube, particularly for chest draining, according to the present disclosure.

With reference to the figures, the coaxial draining tube according to the disclosure, generally designated by the reference numeral 10, comprises substantially an inner tube 15, which has a first opening or cavity 20, and an outer tube 25, which has a second opening or cavity 30, said inner tube 15 being enclosed within said outer tube 25.

In particular, the inner tube 15 has a smaller diameter than the diameter of the cavity 30 of the outer tube 25, such as to maintain between the two tubes 15 and 25 a distance, and consequently a portion of the second opening 30 of the outer tube 25, that is sufficient to allow a stream of air 160 and/or liquids 165.

Since the draining tube 10 is of the coaxial type, a term generally used to reference objects or devices that have an axis in common, the inner tube 15 and the outer tube 25 are mutually integral, so as to maintain indeed a common longitudinal axis.

For this purpose, the inner tube 15 and the outer tube 25 are mutually coupled by way of suitable supporting means, such as for example ridges 35.

In a preferred embodiment of the coaxial draining tube 10, the inner tube 15 and the outer tube 25 are mutually coupled by means of four ridges 35 that extend along the entire length of the coaxial draining tube 10. In practice, the ridges 35 divide the portion of the second opening 30 comprised between the inner tube 15 and the outer tube 25 into four separate channels, which are extended along the entire length of the coaxial draining tube 10, and so do the ridges 35.

The coaxial draining tube 10 according to the disclosure has, along its portion intended to be inserted in the chest cavity 150 of the patient, one or more holes wide enough to allow a stream of air 160 and/or liquids 165. Obviously, the number and/or width of said holes can vary in the several embodiments of the disclosure while remaining within a value that does not affect negatively the structure itself of the coaxial draining tube 10.

In a preferred embodiment of the coaxial draining tube 10, said holes can comprise grooves 40, 45 and 50, which are longitudinal with respect to the coaxial draining tube 10 and are distributed at regular intervals along the portion of the coaxial draining tube 10 designed to be inserted in the chest cavity 150 of the patient.

The grooves 40 and 45 are located in the end portion of the coaxial draining tube 10, i.e., in the portion that will reach the apical region of the pleural space 155 of the chest cavity 150; in particular, the grooves 40 are provided along the surface of the outer tube 25, while the grooves 45 are provided along the surface of the inner tube 15, preferably at the grooves 40.

The grooves 40 and 45, which are present respectively on the surface of the tubes 25 and 15 of the coaxial draining tube 10, allow the passage of the air 160 from the apical region of the pleural space 155 of the chest cavity 150 directly to the opening 20 of the inner tube 15; said inner tube 15 and the corresponding opening 20 are indeed dedicated to the continuous evacuation of the air 160 toward a collecting chamber 110.

The grooves 50, instead, are located after said end portion of the coaxial draining tube 10, i.e., in the portion that will reach the basal region of the pleural space 155 of the chest cavity 150, and are provided along the surface of the outer tube 25.

The grooves 50, present on the surface of the outer tube 25 of the coaxial draining tube 10, allow the passage of the liquids 165 from the basal region of the pleural space 155 of the chest cavity 150 directly to the opening 30 of the outer tube 25, particularly to the channels into which it is divided, said outer tube 25 and the corresponding opening 30 being indeed dedicated to the continuous evacuation of the liquids 165 toward a collecting chamber 110. It should be noted that this passage of the liquids 165 occurs without any contact with the opening 20 of the inner tube 15, which as mentioned evacuates the air 160.

In summary, the opening 20 of the inner tube 15, in particular by way of the grooves 40 and 45 present respectively along the outer tube 25 and along the inner tube 15, is adapted to evacuate continuously the air 160 that has exited from a lung 170 and has accumulated in the apical region of the pleural space 155 of the chest cavity 150, while the opening 30 of the outer tube 25, particularly by way of the grooves 50 present along the outer tube 25, is adapted to evacuate continuously the liquids 165 that have exited from a lung 170 and have accumulated in the basal region of the pleural space 155 of the chest cavity 150.

In a preferred embodiment of the disclosure, the coaxial draining tube 10 can comprise a connector 60 arranged at the opposite end with respect to its end portion provided with holes or grooves 40, 45 and 50, said connector 60 being adapted to combine in a single stream the air 160 conveyed by the inner tube 15 and the liquids 165 conveyed by the outer tube 25.

In a preferred embodiment of the disclosure, the coaxial draining tube 10 can further comprise a tube 65 with a single opening arranged at the end of the connector 60 that lies opposite the tubes 15 and 25, said tube 65 being adapted to convey the stream, comprising both air 160 and liquids 165, produced by the connector 60, and to allow the connection of said coaxial draining tube 10 to an air-liquid separation device 120 or to a manifold tube 115, which in turn is connected to a collecting chamber 110.

In practice, the coaxial draining tube 10 according to the disclosure has the same functional characteristics as a pair of draining tubes currently in use, overcoming however the limitations and drawbacks that derive from the use of a pair of draining tubes instead of a single one.

By way of example, the coaxial draining tube 10 according to the disclosure can be comprised in a chest draining system 100, comprising is further at least one collecting chamber 110, at least one manifold tube 115 and an optional air-liquid separation device 120.

This chest draining system 100, which as mentioned comprises a coaxial draining tube 10 according to the disclosure, has the same functional characteristics as a chest draining system comprising a pair of draining tubes currently in use but overcomes the limitations and drawbacks that derive from the use of a pair of draining tubes instead of just one.

In practice it has been found that the disclosure fully achieves the intended aims and advantages. In particular, it has been shown that the coaxial draining tube, particularly for chest draining systems, thus conceived allows to overcome the quality limitations of the background art, since it allows the simultaneous and continuous evacuation of the fluids, i.e., of air and liquids, present in the chest cavity of the patient, though being used individually.

Another advantage of the coaxial draining tube according to the disclosure resides in that it facilitates a faster expansion of the lung by way of the simultaneous evacuation of air and liquids, with the consequent reduction of the hospitalization times of the patient.

A further advantage of the coaxial draining tube according to the disclosure resides in that it facilitates the management thereof and more generally the management of the chest draining system, and minimizes the intensity of the pain felt by the patient.

Although the coaxial draining tube according to the disclosure has been conceived particularly for chest draining systems, it can be used in any case, more generally, in any system or field in which it is necessary or in any case useful to evacuate separately accumulated air and the liquids.

The coaxial draining tube according to the disclosure can be supplied to any draining system, be it with one or multiple collecting chambers, be it provided or not with valves for the application and adjustment of the suction, be it equipped or not with a vacuum unit or connected to the centralized vacuum system of the hospital. Said coaxial draining tube performs its function regardless of the collecting system to which it is connected.

The disclosure thus conceived is susceptible of numerous modifications and variations; by way of non-limiting example, the person skilled in the art comprises without effort that it is also possible to provide a mechanism or a valve for interrupting the flow of fluids in input or for interrupting the flow of liquids and air in output. All the details may further be replaced with other technically equivalent elements.

In practice, the materials used, as well as the contingent shapes and dimensions, may be any according to requirements and to the state of the art.

The invention claimed is:

1. A coaxial draining tube configured to be used for chest draining systems, the coaxial draining tube comprising:
    an inner tube having a first opening, and
    an outer tube having a second opening, said inner tube being enclosed within said outer tube and having a smaller diameter than said second opening of said outer tube,
    said inner and outer tubes being mutually coupled by way of supporting means and comprising one or more holes adapted to allow the passage of air from the chest cavity to said first opening of said inner tube, wherein said outer tube comprises one or more grooves adapted to allow the passage of liquids from the chest cavity to said second opening of said outer tube, the passage of liquids occurring without any contact with the first opening of the inner tube, said one or more holes and said one or more grooves being provided in the portion of said coaxial draining tube configured to be inserted in the chest cavity of a patient, and further comprising a connector configured to combine in a single stream the air conveyed by said inner tube and the liquids conveyed by said outer tube, wherein said one or more holes are provided in the end portion of said coaxial draining tube, and wherein said one or more grooves are provided following said end portion of said coaxial draining tube.

2. The coaxial draining tube according to claim 1, wherein said supporting means comprise at least one ridge.

3. The coaxial draining tube according to claim 1, further comprising a tube adapted to convey said stream produced by said connector and configured to connect said coaxial draining tube to an air-liquid separation device or to a manifold tube.

4. A chest draining system comprising a coaxial draining tube according to claim 1.

* * * * *